(12) United States Patent
Langholz et al.

(10) Patent No.: US 8,879,072 B2
(45) Date of Patent: Nov. 4, 2014

(54) LASER SCANNING MICROSCOPE AND METHOD FOR OPERATION THEREOF

(75) Inventors: Nils Langholz, Apolda (DE); Dieter Huhse, Berlin (DE)

(73) Assignee: Carl Zeiss Microscopy GmbH, Jena (DE)

( * ) Notice: Subject to any disclaimer, the term of this patent is extended or adjusted under 35 U.S.C. 154(b) by 209 days.

(21) Appl. No.: 13/413,960

(22) Filed: Mar. 7, 2012

(65) Prior Publication Data

US 2012/0229815 A1 Sep. 13, 2012

(30) Foreign Application Priority Data

Mar. 8, 2011 (DE) .......................... 10 2011 013 614

(51) Int. Cl.
| | |
|---|---|
| *G01B 11/24* | (2006.01) |
| *G01N 21/64* | (2006.01) |
| *G06T 5/50* | (2006.01) |
| *G02B 21/00* | (2006.01) |

(52) U.S. Cl.
CPC .......... *G02B 21/008* (2013.01); *G01N 21/6458* (2013.01); *G06T 2207/10144* (2013.01); *G06T 5/50* (2013.01); *G06T 2207/20216* (2013.01); *G06T 2207/20208* (2013.01); *G06T 2207/10061* (2013.01); *G02B 21/0076* (2013.01)
USPC ........ 356/601; 356/600; 250/458.1; 250/205; 359/385; 359/388; 359/368

(58) Field of Classification Search
USPC ................. 356/417, 601, 300; 250/205, 461.2
See application file for complete search history.

(56) References Cited

U.S. PATENT DOCUMENTS

| | | | |
|---|---|---|---|
| 6,167,173 A | 12/2000 | Schoeppe et al. | |
| 6,486,458 B1 | 11/2002 | Schoeppe et al. | |
| 6,563,632 B1 | 5/2003 | Schoeppe et al. | |
| 6,631,226 B1 | 10/2003 | Schoeppe et al. | |
| 7,554,664 B2 * | 6/2009 | Wolleschensky et al. | .... 356/417 |
| 2003/0021018 A1 * | 1/2003 | Birk et al. | ...................... 359/381 |
| 2003/0132394 A1 * | 7/2003 | Wolleschensky et al. | . 250/458.1 |
| 2005/0179892 A1 * | 8/2005 | Gerstner et al. | .............. 356/318 |
| 2006/0011803 A1 * | 1/2006 | Wolleschensky | .......... 250/201.3 |
| 2006/0012856 A1 * | 1/2006 | Wolleschensky | ............. 359/368 |
| 2007/0063153 A1 | 3/2007 | Widzgowski et al. | |
| 2010/0201799 A1 | 8/2010 | Mohrholz et al. | |
| 2011/0215258 A1 * | 9/2011 | Kempe et al. | ............... 250/459.1 |
| 2012/0133889 A1 * | 5/2012 | Bergt et al. | .................... 351/206 |

FOREIGN PATENT DOCUMENTS

| | | |
|---|---|---|
| DE | 197 027 53 | 7/1998 |
| DE | 10 2005 045 163 | 3/2007 |
| DE | 10 2007 046 210 | 4/2009 |
| EP | 1 882 969 | 1/2008 |

* cited by examiner

*Primary Examiner* — Tarifur Chowdhury
*Assistant Examiner* — Isiaka Akanbi
(74) *Attorney, Agent, or Firm* — Frommer Lawrence & Haug LLP

(57) ABSTRACT

Laser scanning microscope and method for the operation thereof having at least two detection channels which has at least one beamsplitter with a splitting of the sample light deviating from the 50:50 split and/or, with 50:50 split in the detection channels, has detectors with differently adjusted gain, or in at least one detection channel with equal light splitting has an additional light attenuator.

19 Claims, 10 Drawing Sheets

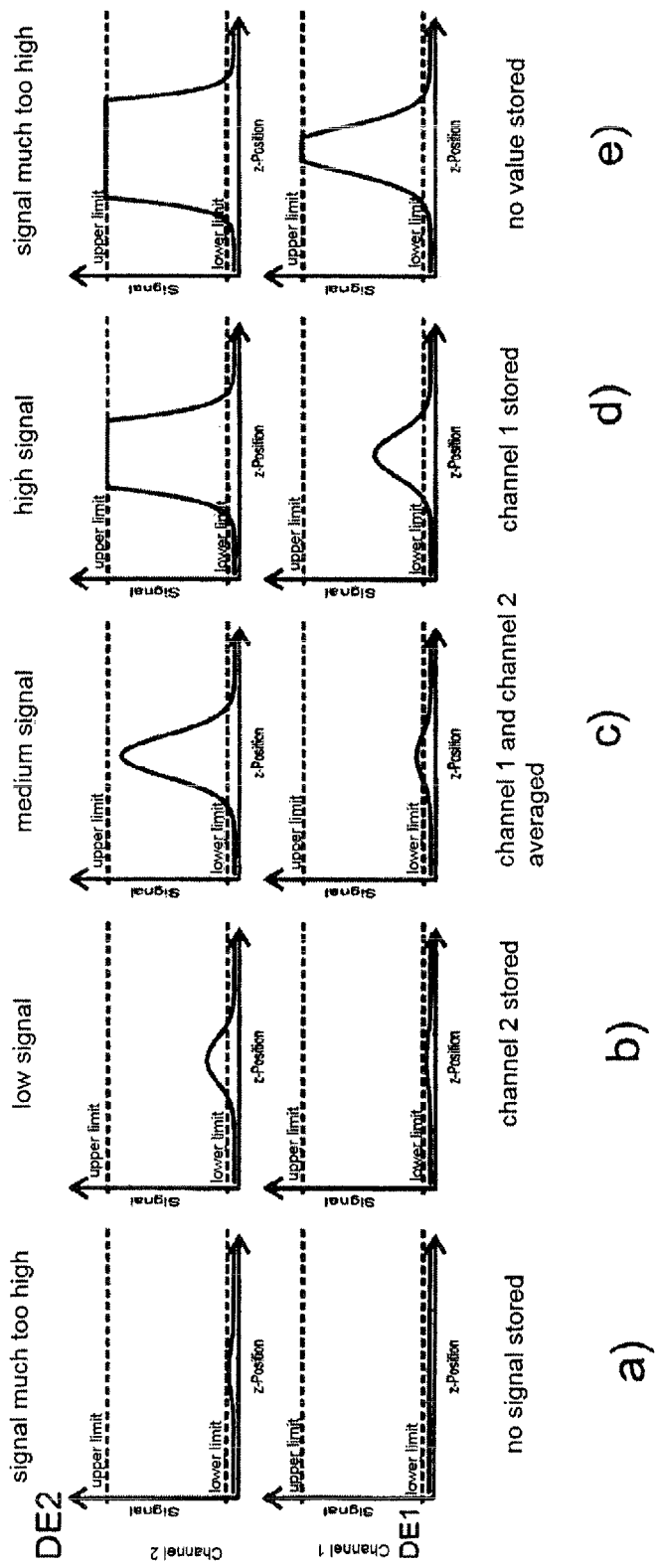

Process Flow

Topography measurement

Fig. 4c

Biomedical Application

A5 | Intensities I (Xi, Yi, Z) compared with Su, So for De1, DE2 for every point x, y, z

- I(Xi, Yi, Z) between So and Su for De1 and De2
- I(Xi, Yi, Z) between So and Su for only one of both De1 and De2
- I(Xi, Yi, Z) less than Su or greater than So for De1 and De2

A6

- Average of De1, De2 taken and stored
- This value is stored
- Su or So stored

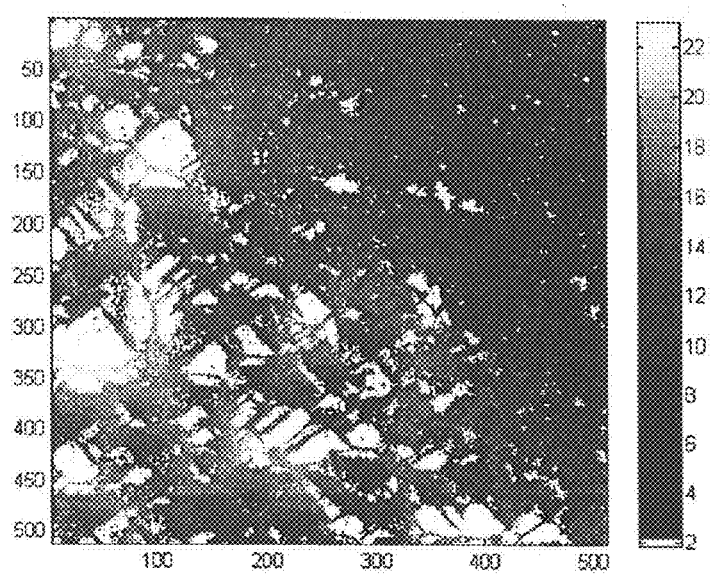
Fig. 6: Topography of a solar cell with electrode channel 1 - optimized to high reflection.

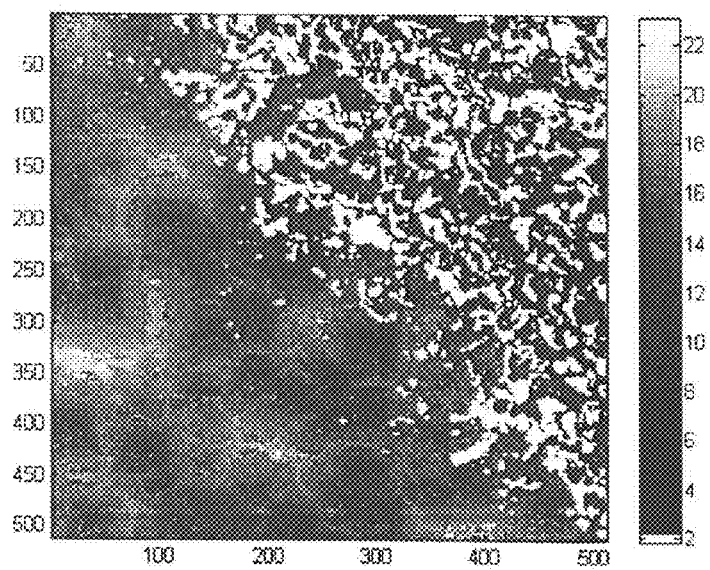
Fig. 7: Topography of a solar cell with electrode channel 2 – optimized to low reflection.

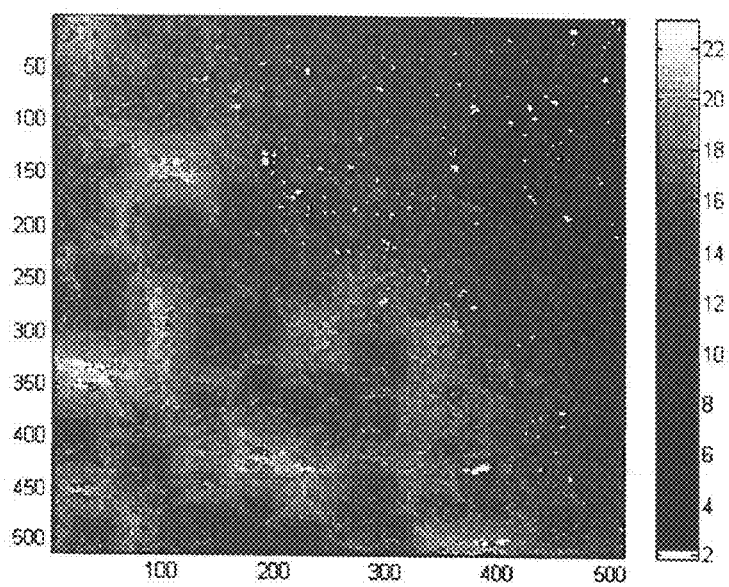
Fig. 8: Topography after calculation of both channels.

US 8,879,072 B2

LASER SCANNING MICROSCOPE AND METHOD FOR OPERATION THEREOF

The present application claims priority from German Patent Application No. DE 10 2011 013 614.2 filed on Mar. 8, 2011, the disclosure of which is incorporated herein by reference in its entirety.

BACKGROUND OF THE INVENTION

Materials samples and biomedical samples frequently have high contrast ratios. These high contrast ratios cannot be covered by a single measurement, for example, with the Zeiss LSM 700. For this purpose, there are HDR (High Dynamic Range) methods in which the measurement result is composed of a number of individual measurements with different illumination intensities or detector sensitivities (PMT gain). However, the measurements are carried out consecutively, which leads to the following problems.

In the field of materials (topography measurement):
Long measuring times. Since scanning must be at least doubled, the measuring time is at least doubled.
The risk that not exactly the same measuring points will be scanned in the individual measurements, e.g., due to vibrations and scanners which do not run in an exact manner.
Calculated height values which are based on evaluation of a PSF with a low intensity generally exhibit noisier performance.

In the biomedical field:
Long measuring times. Since scanning must be at least doubled, the measuring time is at least doubled.
The risk that not exactly the same measuring points will be scanned in the individual measurements, e.g., due to vibrations and scanners which do not run in an exact manner.
The sample is stressed to a greater extent due to the doubled scanning, which can lead to a bleaching of the sample.
When viewing living cells, changes may occur in the cells, i.e., the sample, between individual measurements; that is, combining the observation of living cells with HDR is useful only to a limited extent with present-day methods.

In current methods, a number of measurements are carried out consecutively and then calculated. The individual measurements are sometimes combined to form a measurement sequence which appears outwardly as an individual measurement. Optical elements such as mirror arrays or sensor parameters are then changed between the partial measurements.

For HDR cameras, there are special camera chips which can acquire a greater dynamic range. However, they are not suitable as a substitute for the photomultiplier tubes ("PMTs").

In another field, that of ophthalmology (DE102007046210A1), a fundus image with expanded dynamics is generated by means of a beamsplitter with an asymmetrical splitting ratio and a plurality of image sensors.

SUMMARY OF THE INVENTION

It is the object of the invention to provide methods and arrangements of the type mentioned above which allow a quantitative evaluation of images acquired by microscope with minimal error. In particular, the quantitative evaluation is possible at a high speed.

It is an object of the invention to overcome the above-mentioned problems.

The invention brings about a number of surprising improvements over the prior art:

A color neutral splitter having a high splitting ratio such as 1000:1 or 100:1 can be used. A substantially higher dynamic range of intensity can be acquired in this way.
A color neutral splitter which does not deviate significantly from 50:50 can also be used. In this case, only the gain is available for increasing contrast.
It is not necessary to use only two sensors. With additional beam splitting, additional sensors can be connected either for subsequent spectral dispersion or for further expansion of the dynamic range.
Photomultiplier tubes ("PMTs") need not be used as sensors. In principle, any light-sensitive sensor, e.g., also CCD chips or CMOS chips, can be used.
Measuring adjustment need not be performed manually; automation or partial automation of the measuring conditions can also be implemented.

BRIEF DESCRIPTION OF THE DRAWINGS

FIGS. 3a)-3e) show an X/Y brightness signal corresponding to a picture point along a direction Z resulting from a vertically proceeding recording of images;

FIG. 6 shows the topography of a solar cell with pyramid structure recorded with a first channel;

FIG. 7 shows the topography of a solar cell with pyramid structure recorded with a second channel; and FIG. 8 sows the calculated topography of the two channels from FIGS. 6 and 7.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1:
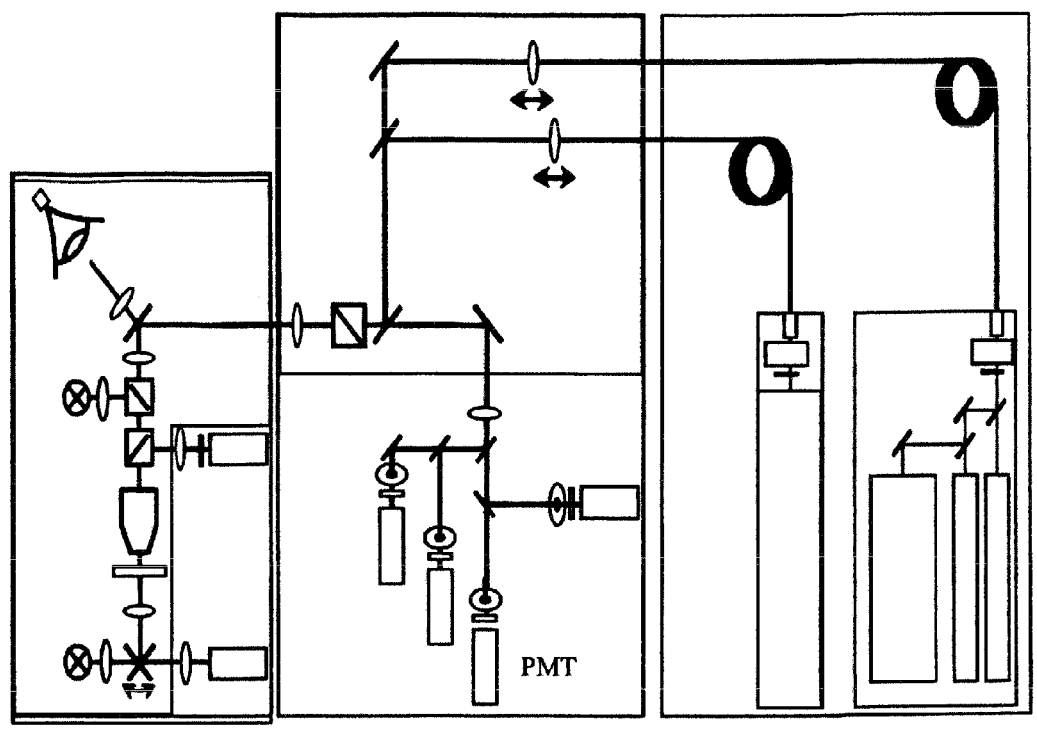
FIG. 1 schematically shows a beam path of a laser scanning microscope.

A beam path of a laser scanning microscope is shown schematically in FIG. 1. As is shown in FIG. 1, a laser scanning microscope ("LSM") is basically made up of a plurality of modules: light source, scanning module, detection unit, and microscope. These modules are described in more detail in the following. In addition, reference is made to DE19702753A1 which is incorporated as reference in the disclosure.

In the LSM, lasers with different wavelengths are used in the light source module. In this regard, different lasers (argon, argon krypton, TiSa lasers) are used. Further, the selection of wavelengths and the adjustment of the intensity of the required excitation wavelength are carried out in the light source module, e.g., using an acousto-optic crystal (AOTF). Subsequently, the laser beam arrives in the scanning module via a fiber or a suitable mirror arrangement.

By means of the objective, the laser radiation generated in the light source is focused in the specimen in a diffraction-limited manner via the scanner, scanning optics and tube lens. The focus scans the sample point by point in x-y direction. The pixel dwell times during the scanning of the sample are usually in the range of less than one microsecond to several hundreds of microseconds.

In confocal detection, the light which is emitted from the focus plane and from the planes situated above and below the latter arrive in a dichroic beamsplitter via the scanner. This dichroic beamsplitter separates the sample light from the excitation light. The sample light is then focused on a diaphragm (confocal diaphragm/pinhole) which is located precisely in a plane conjugate to the focus plane. In this way, light components outside the focus are suppressed. By varying the size of the diaphragm, the optical resolution of the microscope can be adjusted. Another dichroic block filter which further suppresses the illumination radiation is usually located behind the diaphragm. After passing the block filter, the sample light is measured by a point detector (usually a photomultiplier tube ("PMT")). By recording a plurality of optical sections in the x-y plane at different depths z of the sample, a three-dimensional image of the sample can be computer-generated. The LSM is therefore suitable for examining thick specimens.

In biomedical applications, a number of different cell regions are labeled by different dyes simultaneously (multifluorescence). In the prior art, the individual dyes can be detected separately based either on different absorption characteristics or emission characteristics (spectra). Further, an additional splitting of the fluorescent light of a plurality of dyes is carried out with the auxiliary beamsplitters (DBS), and a separate detection of the individual dye emissions is carried out in separate point detectors (e.g., PMTs).

Figure 2:
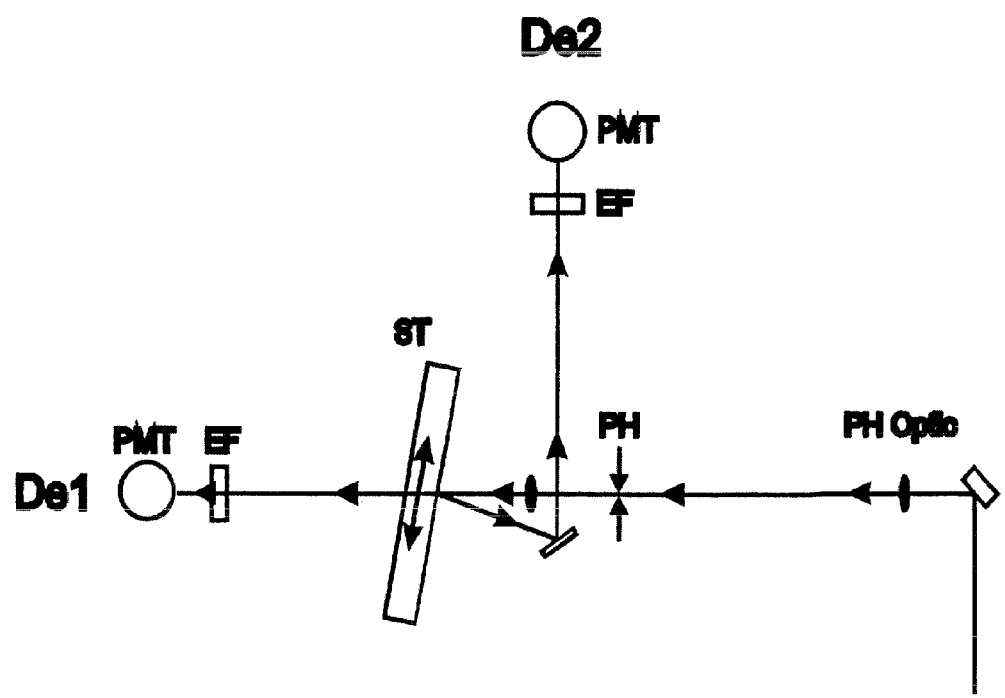
FIG. 2 shows a an extracted view of a partial beam path in an embodiment of a detection arrangement.

FIG. 2 is an extracted view of a partial beam path in the detection arrangement comprising pinhole optics with pinhole arranged therebetween and a partially transmitting beamsplitter ST for partial transmission in direction of a detector DE1, preferably a PMT, and partial reflection by a mirror SP in direction of a detector DE2, preferably a PMT.

For example and without limitation, the beam path in FIG. 2 can take the place of one or more detection beam paths in FIG. 1.

The beamsplitter can be constructed as a 50:50 beamsplitter, but can preferably also have different splitting in directions DE1 and DE2 by means of corresponding coating, for example, 70:30, but also up to 99:1.

In a particularly advantageous manner, the beamsplitter ST is constructed so as to be displaceable (indicated by the arrow) relative to the beam path and has different splitting ratios along its path, for example, by means of different coatings; these splitting ratios can be formed discretely but also so as to pass into one another continuously so that, depending on the application, the splitting ratio can be changed continuously or discretely by displacing ST at an angle to the detection beam path.

In case of a 50:50 percent configuration of the beamsplitter, either the sensitivity of the two detectors (PMT) is adjusted differently or the split beam is reduced in one of the beam paths to DE1 and DE2, for example, by means of a reduction in transmission.

With the aid of a flowchart, FIG. 4 shows how the inventive advantageous evaluation of detector channels DE1, DE2 in combination with the sample scanning is carried out by means of the laser scanning microscope.

As is well known, a point-by-point scanning of the sample by an illumination beam is generated by means of the LSM and the scanner thereof and the reflection signals or fluorescence signals corresponding to these illuminated points are acquired and associated with the respective picture point and stored as X values and Y values. Accordingly, an image is formed from a stored X/Y detection distribution. By moving the sample or the objective in (vertical) Z direction, these X/Y image distributions are recorded for different z values so that an X/Y/Z stack of images results after passing in Z direction and scanning in X/Y direction.

According to the illustration in FIG. 2, the recording is now carried out in a parallel manner with detectors DE1 and DE2 so that two separate image stacks which are associated with one another point by point are present in the image storage for these two detection channels.

Instead of letting the individual measurements take place consecutively; the measurements take place simultaneously according to the invention. The detection light is split to two different detectors with a sharply differing splitting ratio (e.g., 100 to 1). With suitably selected PMT gain, the weak signal components can be made clearly visible in one channel, but the stronger signal components are overexposed or overdriven. However, these strong signal components are correctly measured in the second channel which is adjusted in such a way that there is no overexposure. In a final step, the two signals can then be combined and suitably calculated so as to obtain an image with higher dynamics or a topography image with fewer voids than each individual detector by itself would allow.

In calculating the topography of a surface to be measured, the following procedure is usually followed:
1) Z stack is recorded; a plurality of two-dimensional (x/y) image signals are obtained for the different z positions;
2) the brightness-over-z curve is generated for every x-y picture point (see, e.g., FIG. 3);
3) the position of the maximum is found; this then represents the z position of the surface at location x-y.

When only one detector is used, only the limited dynamic range is available which is represented, e.g., in Illustration 1, by the upper limit and lower limit lines.

Further details are described more fully particularly with reference to FIGS. 3 and 4.

An X/Y brightness signal corresponding to a picture point along a direction Z resulting from a vertically proceeding recording of images (see above) is shown in FIGS. 3a-e by way of example for the two detection channels DE1, DE2.

Set threshold values So and Su which depend on the detector being used, for example, the PMT being used and the measuring range thereof, are shown. A relatively low maximum in 3b is registered only by detector DE2; in DE1, it lies below the lower threshold value Su.

In 3c, a signal within the threshold value is registered by both detectors DE1 and DE2. In FIG. 3d, the signal in DE2 is so high that it lies above the upper threshold value; a signal is determined only in channel 1 (DE1).

In 3a, the signal falls below the lower threshold value in both DE1 and DE2; in 3e, the signal exceeds the upper threshold value in both channels.

Figure 4A:
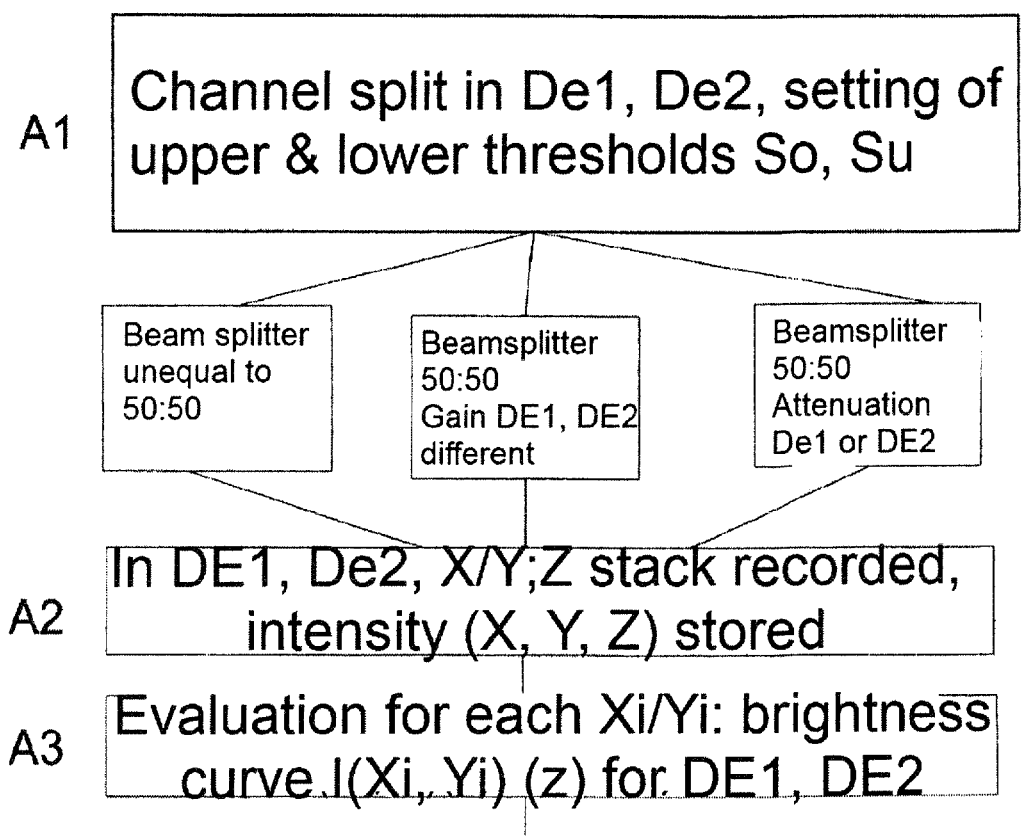
FIG. 4 is a flowchart showing how the inventive advantageous evaluation of detector channels DE1, DE2 in combination with the sample scanning is carried out by means of the laser scanning microscope.
Figure 4B:
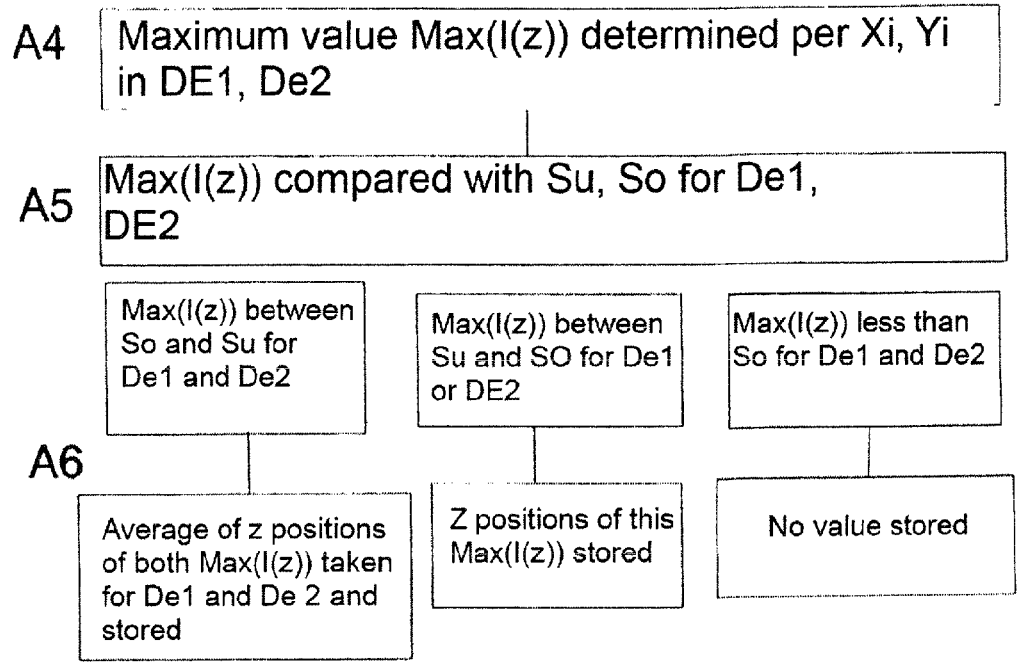

The procedure is also described in more detail with reference to the flowchart in FIG. 4. FIG. 4a shows the steps A1-A3 common to both biomedical image recordings and topography recordings. FIG. 4b shows the sequence in A4-A6 in topography measurement, and FIG. 4c) shows steps A5, A6 in biomedical imaging.

1. The light is split into (at least) two channels so that there is a higher signal, e.g., in channel 2 than in channel 1 (step A1 in FIG. 4). For this purpose (A1 in FIG. 4), e.g., the light can be split with a ratio unequal to 50:50 (e.g., 99:1) to equally sensitive detectors;
   a. or, in case of a 50:50 split, the sensitivities of the two channels or, in PMTs, the gain of the two channels, are selected differently;
   b. or one of the two channels is attenuated by a neutral filter or the like;
   c. or a combination of 2 or 3 from the above is carried out.
2. A z stack is recorded (step A2 in FIG. 4); a plurality of 2-channel-2D(x/y) image signals are obtained for the different z positions.
3. The brightness-over-z curve is generated individually for each x-y picture point for each channel DE1, DE2 (FIG. 3 and A3 in FIG. 4).
4. The z position of the maximum is determined (A4 in FIG. 4) for each x-y point for each channel.
5. The signal curves (FIG. 3) are compared with the set threshold values (A5 in FIG. 4) and the applicable z position is selected for point x-y according to the following scheme (A6 in FIG. 4):
   a. If the found maximum or the intensity is greater than the lower limit and less than the upper limit for only one of the two channels, only the z position of the maximum or of the intensity is then selected from this channel (FIGS. 3b, 3d).
   b. If the found maximum or the intensity is greater than the lower limit and less than the upper limit for both channels, the z position of the maximum or intensity is then selected as an average of the z positions of the maxima or intensities of both channels (FIG. 3c). A different weighting, e.g., according to intensity for reducing the signal-to-noise ratio is also conceivable in this case.
   c. If the found maximum or the intensity is greater than the lower limit and less than the upper limit for neither of the two channels (both channels are overdriven or underdriven), then the z position cannot be determined for these x-y positions (so-called void or hole) (FIGS. 3a, 3e).

When the splitting, either of light or sensitivities, is suitably selected, greater total dynamics are obtained. In this case, it is additionally advantageous that knowledge of the exact splitting factor or even a calibration of the two channels relative to one another is not necessary.

Naturally, e.g., when using PMTs, optimal ratios can be achieved by means of pre-calibration and subsequent suitable selection of the two PMT high voltages in order to obtain the greatest effective dynamic range. The high voltage of channel 2 could then be set automatically, e.g., when the high voltage of channel 1 is selected by the user. The gain of a PMT depends upon the applied high voltage and is therefore used synonymously herein.

Figure 5:
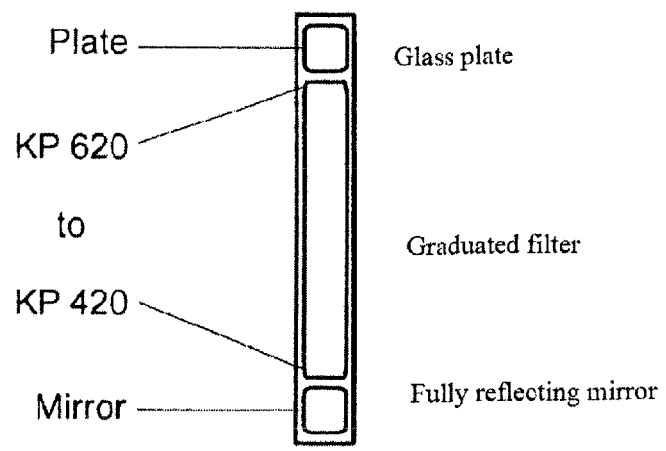
FIG. 5 shows an embodiment using a graduated filter (VSD slide) provided in a laser scanning microscope.

Surprisingly, a graduated filter (VSD slide), shown in FIG. 5, which is provided in the LSM 700 can now also be used according to the invention. In addition to a middle portion with a variable spectrum graduated filter at its edge, this graduated filter (see also EP1882969 A1) has a glass plate which was used heretofore to effectively "switch off" the graduated filter. It has a fully reflecting mirror (mirror) at its other edge.

If the graduated filter is now displaced in the beam path until the glass plate arrives in the optically active beam path, the glass plate can surprisingly be used as beamsplitter ST as described in FIGS. 2, 3 by its splitting ratio of approximately 99:1.

The gain for the two channels should be selected in such a way that overexposures do not occur in the 1-% channel. The gain of the 99-% channel should be selected in such a way that there are enough voxels which are neither overexposed nor underexposed in the two channels.

An overview image stack is preferably recorded initially and the occurring maximum and minimum intensity is determined. The overview stack can also be carried out with lower resolution (fewer X/Y or Z points are displayed).

During the actual measurement, measuring is carried out with both channels simultaneously. The calculation of the two individual channels to one channel takes place following the measurement.

During the actual fusion of the measurement data, biomedical evaluations and topography evaluations can be advantageously distinguished. The two approaches are described in the following.

In biomedical evaluations, prior calibration of the measurement system is advantageous, particularly for the beamsplitter which is used and possibly for the wavelength dependency thereof or for the differently adjusted detector gain, and the measurement is then evaluated in a wavelength-dependent manner.

In contrast to the view shown in FIG. 3, as a rule, there is no measured value that is not taken into account in these evaluations; rather, low values are multiplied by a factor so that they can be included when determining an average. With a splitting ratio or a gain ratio of 99:1 between DE1 and DE2, for example, the value in channel DE2 is multiplied by 99 and only then is the average formed from DE1 and DE2. This factor can be adjusted in a wavelength-dependent manner in order to produce the same image conditions for all wavelengths.

In topography measurements, the height evaluation is advantageously carried out separately for every x,y coordinate. Channel assignment should be oriented towards height evaluation. This is shown in FIGS. 6-8. FIG. 6 was recorded with channel 1 in FIG. 2 and with channel 2 in FIG. 7. The calculated image is shown in FIG. 8.

FIG. 6 shows the topography of a solar cell with pyramid structure. An electrode of the solar cell can be seen in the upper right-hand area of the image. This electrode has a very high reflectivity in contrast to the solar cell matrix. The first channel was adjusted based on an overview image in such a way that the brightest reflections on the electrode lie within the dynamic range of the PMT. The white areas (particularly at lower left) show the places where there is too little (or too much) light for a useful evaluation.

The adjustment of the channel is carried out, for example, in that in addition to the (for example) 99:1 split between channel 1 and channel 2, a change in gain, for example, for channel 1, is carried out so that this channel has a sensitivity which is, for example, ten times higher than the other channel so that at a splitting ratio of 99:1 a ratio of about 1000:1 is adjusted between the two channels through the change in sensitivity in order to include as many picture points as possible in the applicable area between Su and So so that a picture point can be formed in the calculated image.

The topography of the solar cell is shown again in FIG. 7. The difference between FIG. 6 and FIG. 7 is that measurement was carried out with the second channel. The channel splitting was carried out by the mirror position of the VSD slide. The second channel was adjusted as was described above in such a way that there is another overlapping area at the applicable pixels for the subsequent calculation. The overexposed or underexposed pixels are again identified by white in FIG. 7. The measurements in the two channels took place simultaneously.

It will be seen that other areas are void in both images; in FIG. 6 chiefly because the pixels were too dark, and in FIG. 7 chiefly because they were overdriven.

The calculated topography of the two channels is shown in FIG. 8. In the calculation, the average of the two height values was calculated in the common applicable area of the two channels. When there was only one applicable height value, this was used. The white positions in the image show the locations in which there is an overexposure or underexposure on both channels. The example shows the case of a fast measurement and no scenario with optimized measuring conditions. Accordingly, further improvements are possible.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A method for operating a laser scanning microscope, the method comprising:
   carrying out a two-dimensional horizontal image scanning in a plurality of focus positions or height positions;
   detecting, accordingly in a channel of each of at least two detectors, the sample light;
   recording three-dimensional image stacks simultaneously with the at least two detectors;
   splitting the sample light unequally between the at least two detectors with a color neutral beamsplitter; and
   calculating, for individual picture points and an associated height position, a measured intensity value of each of the two detector channels by picture point;
   wherein, when each of the two intensity values lies within a threshold region of the respective detector channel, a sample image is generated from the two calculated intensity values in that an average is formed between the two intensity values;
   wherein, when only one of the two intensity values lies within a threshold region of the respective detector channel, a sample image is generated from only one of the two intensity values; and
   wherein, when neither of the two intensity values lies within a threshold region of the respective detector channel, a sample image is generated using neither of the two intensity values.

2. The method according to claim 1;
   wherein a splitting ratio of the unequal splitting is adjustable.

3. The method according to claim 1;
   wherein the at least one color neutral beamsplitter deviating from a 50:50 split is provided in the detection beam path for the unequal splitting.

4. The method according to claim 3;
   wherein the at least one color neutral beamsplitter has areas with different splitting ratios and is displaceable in the beam path relative to the optical axis.

5. The method according to claim 1;
   wherein photomultiplier tubes are provided in the detection channels.

6. The method according to claim 1;
   wherein a detector gain is controlled differently for each of the two detection channels.

7. The method according to claim 6;
   wherein the detector gain is controlled differently for each of the two detection channels depending on the measured intensity distribution.

8. The method according to claim 1;
   wherein an overview image stack is recorded for at least one of:
      adjusting a splitting ratio of the unequal splitting of the sample light; and
      adjusting a detection gain of each of the two detector channels.

9. The method according to claim 1;
   wherein intensity maxima or centroids of an intensity distribution are used as intensity values; or
   wherein a value obtained from the intensity curve according to an algorithm for topography measurement is used as an intensity of at least one of the two detector channels.

10. A control unit for a laser scanning microscope, the control unit being configured to read out at least two detection channels and to carry out the method of claim 1.

11. A laser scanning microscope comprising:
    a control unit according to claim 10 with at least two detection channels; and
    at least one color neutral beamsplitter which splits the sample light at least one of:
       ratio deviating from a 50:50 split; and
       a 50:50 split in the detection channels;
    wherein, when the beamsplitter splits the sample light at a 50:50 split, the laser scanning microscope further includes:
       detectors with differently adjusted gain; or
       detectors with the same gain, and a light attenuator in at least one detection channel.

12. A method for operating a laser scanning microscope, the method comprising:
    carrying out a two-dimensional horizontal image scanning in a plurality of focus positions or height positions;
    detecting, accordingly in a channel of each of at least two detectors, the sample light, wherein the sample light is split unequally with at least one color neutral beamsplitter;
    recording three-dimensional image stacks simultaneously with the at least two detectors having different gains; and
    calculating, for individual picture points and an associated height position, a measured intensity value of each of the two detector channels by picture point;
    wherein, when each of the two intensity values lies within a threshold region of the respective detector channel, a sample image is generated from the two calculated intensity values in that an average is formed between the two intensity values;
    wherein, when only one of the two intensity values lies within a threshold region of the respective detector channel, a sample image is generated from only one of the two intensity values; and
    wherein, when neither of the two intensity values lies within a threshold region of the respective detector channel, a sample image is generated using neither of the two intensity values.

13. The method according to claim 12;
    wherein photomultiplier tubes are provided in the detection channels.

14. The method according to claim 12;
    wherein a detector gain is controlled differently for each of the two detection channels.

15. The method according to claim 14;
wherein the detector gain is controlled differently for each of the two detection channels depending on the measured intensity distribution.

16. The method according to claim 12;
wherein an overview image stack is recorded for adjusting a detection gain of each of the two detector channels.

17. The method according to claim 12;
wherein intensity maxima or centroids of an intensity distribution are used as intensity values; or
wherein a value obtained from the intensity curve according to an algorithm for topography measurement is used as an intensity of at least one of the two detector channels.

18. A laser scanning microscope comprising:
a control unit according to claim 17 with at least two detection channels; and
at least one color neutral beamsplitter which splits the sample light at least one of:
  ratio deviating from a 50:50 split; and
  a 50:50 split in the detection channels;
wherein, when the beamsplitter splits the sample light at a 50:50 split, the laser scanning microscope further includes:
  detectors with differently adjusted gain; or
  detectors with the same gain, and a light attenuator in at least one detection channel.

19. A control unit for a laser scanning microscope, the control unit being configured to read out at least two detection channels and to carry out the method of claim 12.

* * * * *